US010309888B2

(12) United States Patent
Saeda et al.

(10) Patent No.: US 10,309,888 B2
(45) Date of Patent: Jun. 4, 2019

(54) BIOSENSOR COMPRISING ELECTRODE FOR MEASURING HEMATOCRIT VALUE

(71) Applicant: ARKRAY, Inc., Kyoto (JP)

(72) Inventors: Megumi Saeda, Kyoto (JP); Hisashi Kaneda, Kyoto (JP)

(73) Assignee: ARKRAY, Inc., Kyoto (JP)

(*) Notice: Subject to any disclaimer, the term of this patent is extended or adjusted under 35 U.S.C. 154(b) by 68 days.

(21) Appl. No.: 15/090,649

(22) Filed: Apr. 5, 2016

(65) Prior Publication Data
US 2016/0290910 A1 Oct. 6, 2016

(30) Foreign Application Priority Data

Apr. 6, 2015 (JP) ................................. 2015-077652

(51) Int. Cl.
*G01N 27/327* (2006.01)
*G01N 15/05* (2006.01)
(Continued)

(52) U.S. Cl.
CPC ............. *G01N 15/05* (2013.01); *C12Q 1/006* (2013.01); *G01N 27/028* (2013.01);
(Continued)

(58) Field of Classification Search
None
See application file for complete search history.

(56) References Cited

U.S. PATENT DOCUMENTS 5,120,420 A * 6/1992 Nankai .................. C12Q 1/001
 204/403.11
6,770,190 B1 8/2004 Milanovski et al.
(Continued)

FOREIGN PATENT DOCUMENTS

EP 3076167 A1 * 10/2016 ............. C12Q 1/006
JP 4341032 B2 10/2009
(Continued)

OTHER PUBLICATIONS

F. Arslan, et al. "An amperometric biosensor for glucose determination prepared from gluocse oxidase immobilized in polyaniline-polyvinylsulfonate film" Sensors, vol. 11, No. 8, Aug. 2011, p. 8152-8163.*
(Continued)

Primary Examiner — J. Christopher Ball
(74) Attorney, Agent, or Firm — Morgan, Lewis & Bockius LLP

(57) ABSTRACT

Provided is a method for measuring the concentration of a substance in a blood sample, the method comprising the steps of: supplying the blood sample to a biosensor comprising a hematocrit electrode for measuring a hematocrit value on the surface of which electrode an electrically conductive polymer is coated by physical adsorption in the absence of a crosslinking agent; and calculating the concentration of the substance from the measured value of a first current resulting from application of a first voltage; and correcting the concentration of the substance with the value of a second current resulting from application of a second voltage or the hematocrit value calculated from the value of the second current.

12 Claims, 3 Drawing Sheets

(51) Int. Cl.
  *G01N 27/02* (2006.01)
  *C12Q 1/00* (2006.01)
  *G01N 27/416* (2006.01)
  *G01N 15/00* (2006.01)

(52) U.S. Cl.
  CPC ..... *G01N 27/3272* (2013.01); *G01N 27/3273* (2013.01); *G01N 27/3274* (2013.01); *G01N 27/4166* (2013.01); *G01N 2015/0065* (2013.01); *G01N 2015/055* (2013.01)

(56) References Cited

U.S. PATENT DOCUMENTS

| | | | |
|---|---|---|---|
| 2006/0042361 | A1 | 3/2006 | Yamaoka et al. |
| 2009/0321277 | A1* | 12/2009 | Heller ............... C12Q 1/006 205/778 |
| 2010/0206749 | A1* | 8/2010 | Choi ............... G01N 27/3274 205/777.5 |
| 2013/0062221 | A1 | 3/2013 | Cai et al. |
| 2016/0025674 | A1* | 1/2016 | Fujiwara ......... G01N 27/3274 204/403.14 |
| 2016/0177365 | A1 | 6/2016 | Katsuki |
| 2016/0290987 | A1 | 10/2016 | Saeda et al. |

FOREIGN PATENT DOCUMENTS

| | | |
|---|---|---|
| JP | 2013-061336 A | 4/2013 |
| WO | 2015/020149 A1 | 2/2015 |

OTHER PUBLICATIONS

K. M. Molapo, et al. "Electronics of Conjugated Polymers (I): Polyaniline" International Journal of Electrochemical Science, vol. 7, p. 11859-11875. (Year: 2012).*

K. Grennan, et al. "Optimisation and characterisation of biosensors based on polyaniline" TALANTA, 68(5):p. 1591-1600, Feb. (Year: 2006).*

D. Zhai, et al. "Highly Sensitive Glucose Sensor Based on Pt Nanoparticle/Polyaniline Hydrogel Heterostructures" ACS NANO, 7(4): p. 3540-3546, Mar. (Year: 2013).*

Extended European Search Report issued in corresponding European Patent Application No. 16163918.2 dated Aug. 8, 2016.

Office Action and Search Report issued in corresponding Chinese Patent Application No. 201610208259.4 dated Dec. 26, 2018.

Samuelson et al., "Biologically Derived Conducting and Water Soluble Polyaniline," Macromolecules, 31: 4376-4378 (1998).

Malhotra et al., "Biosensors for clinical diagnostics industry," Sensors and Actuators B, 91: 117-127 (2003).

* cited by examiner

BIOSENSOR COMPRISING ELECTRODE FOR MEASURING HEMATOCRIT VALUE

TECHNICAL FIELD

The present invention relates to a biosensor comprising an electrode for measuring hematocrit value (hereinafter, simply referred to as hematocrit electrode).

BACKGROUND ART

In biosensors used in blood glucose self-monitoring devices, the value of the current response varies depending on the value of hematocrit in whole blood. It has been an issue that a blood glucose level deviating from its true value may be obtained as a measurement result (hematocrit influence). In view of the hematocrit influence, JP 2013-061336 A discloses a method in which the hematocrit value is measured by applying an alternating voltage in a blood glucose self-monitoring device. The measured hematocrit value is then used to correct the value of the glucose level, so that the deviation from the true value is reduced. Further, JP 4341032 B discloses a method in which a separation membrane is used to separate blood plasma from whole blood, and the blood glucose level in the plasma is then measured in order to prevent the measured glucose level from being affected by the hematocrit value.

However, the method disclosed in JP 2013-061336 A has problems in that the application of alternating voltage increases the electric power consumption by the device, and the accuracy of the blood glucose measurement may be reduced because of overcorrection due to high noise in the measurement of the hematocrit value. Further, in the method disclosed in JP 4341032 B, there are problems in that the structure of a sensor for use in the method may be complex since the sensor requires a separation membrane, and the ability of the separation membrane to separate blood cells may not be stable because of the influence of the viscosity of the sample due to components other than blood cells, such as lipids.

SUMMARY OF THE INVENTION

The present invention has been devised to solve the above-mentioned problems. Therefore, an object of the present invention is to provide a system and method by which the hematocrit value of a blood sample can be easily measured, and the concentration of a substance to be measured, such as glucose, in the sample can be accurately measured by correcting the concentration of the substance with the hematocrit value.

In order to achieve the above mentioned object, one aspect of the present invention relates to a biosensor comprising a hematocrit electrode and an electrically conductive polymer coated on the surface of the hematocrit electrode by physical adsorption. The electrically conductive polymer is preferably a water-soluble electrically conductive polymer. More preferably, the electrically conductive polymer is polyaniline.

Another aspect of the present invention relates to a biosensor comprising the above-mentioned hematocrit electrode, a working electrode, a counter electrode and a reference electrode. The working electrode is preferably an enzyme electrode. More preferably, the enzyme is an oxidoreductase.

Another aspect of the present invention relates to a method for measuring the concentration of a substance in a blood sample, comprising:
supplying the blood sample to a biosensor comprising the above-mentioned hematocrit electrode, a working electrode, a counter electrode and a reference electrode;
measuring the value of a first current which flows when a voltage of 0 to 400 mV is applied to the working electrode, and calculating the concentration of the substance from the measured value of the first current;
measuring the value of a second current which flows when a voltage of 100 to 300 mV is applied to the hematocrit electrode; and
correcting the concentration of the substance with the value of the second current or a hematocrit value calculated from the value of the second current.

Another aspect of the present invention relates to a measuring apparatus comprising:
a biosensor comprising the above-mentioned hematocrit electrode, a working electrode, a counter electrode and a reference electrode;
a control section configured to control the application of voltage to the working electrode and the hematocrit electrode of the biosensor;
a detection section configured to measure the value of a first current which flows when a first voltage is applied to the working electrode, and the value of a second current which flows when a second voltage is applied to the hematocrit electrode;
an arithmetic section configured to calculate the concentration of a substance from the value of the first current, and to correct the calculated concentration of the substance with the value of the second current or, alternatively, a hematocrit value calculated from the value of the second current; and
an output section configured to output the corrected concentration of the substance.

Another aspect of the present invention relates to a method for measuring a hematocrit value of a blood sample, comprising:
supplying the blood sample to a biosensor comprising a hematocrit electrode and an electrically conductive polymer coated on the surface of the hematocrit electrode by physical adsorption; and
measuring the value of a current which flows when a voltage of 100 to 300 mV is applied to the hematocrit electrode.

Another aspect of the present invention relates to a measuring apparatus comprising:
a biosensor comprising a hematocrit electrode and an electrically conductive polymer coated on the surface of the hematocrit electrode by physical adsorption;
a control section configured to control the application of voltage to the hematocrit electrode of the biosensor;
a detection section configured to measure the value of a current which flows when a voltage is applied to the hematocrit electrode;
an arithmetic section configured to calculate a hematocrit value from the measured value of the current; and
an output section configured to output the calculated hematocrit value.

The invention also extends to the use of a biosensor comprising a hematocrit electrode, a working electrode, a counter electrode and a reference electrode (as described herein) or a measuring apparatus comprising the biosensor (as described herein) to measure the concentration of a substance in a blood sample. The invention additionally extends to the use of a biosensor comprising a hematocrit electrode (as described herein) or a measuring apparatus comprising the biosensor (as described herein) to measure a hematocrit value of a blood sample.

According to the present invention, it is possible to easily and accurately measure the hematocrit value of a blood sample, and to obtain a more accurate concentration of a substance, such as a blood glucose level, by correcting the concentration with the hematocrit value.

Figure 1:
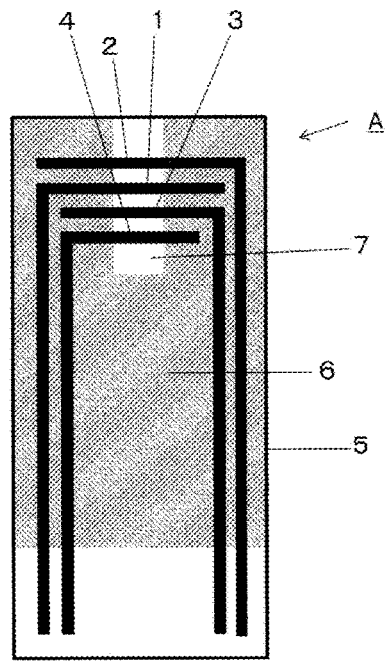
FIG. 1 is a schematic diagram illustrating the structure of a biosensor according to one embodiment of the present invention.

EMBODIMENTS FOR CARRYING OUT THE INVENTION (Hematocrit Electrode)

The hematocrit electrode according to the present invention is an electrode in which an electrically conductive polymer is bound to the surface of the electrode by physical adsorption. The electrically conductive polymer is physically adsorbed on the surface of an electrode surface without being mediated by a crosslinking agent. That is, the electrically conductive polymer is attached to the electrode surface via a non-covalent bond, e.g., by Van der Waals' forces.

(Electrode)

The hematocrit electrode is composed of a metallic material such as gold (Au), platinum (Pt), silver (Ag), or palladium (Pd), or a carbon material such as carbon. The hematocrit electrode is formed, for example, on an insulating base plate. The insulating base plate is composed of an insulating material, and examples thereof include various types of resins (plastics), such as thermoplastic resins (for example, polyetherimide (PEI), polyethylene terephthalate (PET) and polyethylene (PE)); polyimide resins and epoxy resins; glasses; ceramics; papers; and the like. The size and the thickness of the hematocrit electrode and the insulating base plate can be selected as appropriate.

(Electrically Conductive Polymer)

Examples of the electrically conductive polymer to be coated on the surface of the hematocrit electrode by physical adsorption include: polyaniline, polypyrrole, polystyrene sulfonate, polythiophene, polyisothianaphthene, polyethylenedioxythiophene(poly(3,4-ethylenedioxythiophene)poly (styrene sulfonate)), polyacrylamide sulfonate, polyvinyl sulfonate, combinations thereof, and the like. Among these, an electrically conductive polymer which can be dissolved into water to form an aqueous solution is preferred. Polyaniline is more preferred.

Examples of the commercially available products of the electrically conductive polymer as described above specifically, examples of commercially available product of polyaniline include "AQUAPASS 01-x" (manufactured by Mitsubishi Rayon Co., Ltd.). Examples of commercially available polypyrrole products o include "SSPY" (ethyl 3-methyl-4-pyrrolecarboxylate) (manufactured by KAKEN INDUSTRY Co., Ltd.). Examples of commercially available polystyrene sulfonate products include "Poly-NaSS" (manufactured by TOSOH ORGANIC CHEMICAL CO., LTD.). Examples of commercially available polythiophene products include "Espacer 100" (manufactured by TA Chemical Co., Ltd.). Examples of commercially available polyisothianaphthene products include "Espacer 300" (manufactured by TA Chemical Co., Ltd.). Examples of the commercially available polyethylenedioxythiophene(poly(3,4-ethylenedioxythiophene)poly (styrene sulfonate)) products of polyethylenedioxythiophene(poly(3,4-ethylenedioxythiophene) poly (styrene sulfonate)) include "PEDOT-PSS" (Polyscience Inc.).

(Method for Preparing Hematocrit Electrode)

The hematocrit electrode is prepared, for example, as follows. Specifically, a metal layer which functions as an electrode is formed on one surface of the insulating base plate. For example, a metal layer having a desired thickness (for example, about 30 nm) is formed by depositing a metallic material, by physical vapor deposition (PVD, for example, sputtering) or chemical vapor deposition (CVD), on one surface of the insulating base plate which is in the form of a film having a predetermined thickness (for example, about 100 μm). It is also possible to form an electrode layer composed of a carbon material, instead of a metal layer. Next, a layer of the electrically conductive polymer is formed on the electrode. First, a solution (reagent) of the electrically conductive polymer is prepared. The solution (reagent) is dropped on the surface of the electrode. Then the solution (reagent) is allowed to dry and solidify on the electrode, to obtain the hematocrit electrode to the surface of which the electrically conductive polymer is adsorbed.

The hematocrit electrode may include a component(s) other than the electrically conductive polymer. However, even when other component(s) are included, a crosslinking agent is not to be included in the hematocrit electrode.

(Biosensor)

The biosensor according to the present invention includes the hematocrit electrode according to the present invention.

The biosensor according to the present invention may include the hematocrit electrode according to the present invention alone. However, in a more preferred embodiment of the biosensor according to the present invention, the biosensor includes a counter electrode, a working electrode (enzyme electrode), and a reference electrode, along with the hematocrit electrode according to the present invention. The counter electrode, which is used as a pair with the hematocrit electrode, may be any electrode which can be generally used as a counter electrode in a biosensor. Examples of the counter electrode include a carbon electrode prepared in the form of a film by screen printing; a metal electrode prepared in the form of a film by physical vapor deposition (PVD, for example, sputtering) or chemical vapor deposition (CVD); and a silver/silver chloride electrode prepared in the form of a film by screen printing. Further, the reference electrode, which is used as a pair with the working electrode (enzyme electrode) as described herein, may also be the silver/silver chloride electrode; the carbon electrode prepared in the form of a film by screen printing; or the metal electrode prepared in the form of a film by physical vapor deposition (PVD, for example, sputtering) or chemical vapor deposition (CVD).

Next, the working electrode (enzyme electrode) will be described.

(The Structure of Enzyme Electrode)

The enzyme electrode can be prepared by forming a detection layer comprising an enzyme, the above mentioned electrically conductive polymer, a crosslinking agent, and electrically conductive particles as required, on an electrode.

(Enzyme Electrode)

As with the hematocrit electrode, the enzyme electrode is made of a metallic material such as gold (Au), platinum (Pt), silver (Ag) or palladium (Pd); or a carbon material such as carbon. The electrode is formed, for example, on an insulating base plate. The insulating base plate is made of an insulating material, and examples thereof include various types of resins (plastics), such as thermoplastic resins (for example, polyetherimide (PEI), polyethylene terephthalate (PET) and polyethylene (PE)), polyimide resins and epoxy resins; glasses; ceramics; papers; and the like. Any suitable known material can be used as an electrode material for forming the electrode and a material for forming the insulating base plate. The size and the thickness of the electrode and the insulating base plate can be selected as appropriate.

(Detection Layer)

The detection layer of the enzyme electrode is in contact with the electrode, and contains an enzyme, the electrically conductive polymer described in the section of the hematocrit electrode, and a crosslinking agent, and it may also contain other component(s) such as electrically conductive particles. However, it is preferred that the detection layer does not contain an electron mediator.

(Enzyme)

The enzyme can be selected as appropriate depending on a substance to be measured, and examples thereof include oxidoreductases. Examples of oxidoreductases include glucose oxidase (GOD), galactose oxidase, bilirubin oxidase, pyruvic acid oxidase, D- or L-amino acid oxidase, amine oxidase, cholesterol oxidase, choline oxidase, xanthine oxidase, sarcosine oxidase, L-lactic acid oxidase, ascorbic acid oxidase, cytochrome oxidase, alcohol dehydrogenase, glutamic acid dehydrogenase, cholesterol dehydrogenase, aldehyde dehydrogenase, glucose dehydrogenase (GDH), fructose dehydrogenase, sorbitol dehydrogenase, lactic acid dehydrogenase, malic acid dehydrogenase, glycerol dehydrogenase, 17β hydroxysteroid dehydrogenase, estradiol 17β dehydrogenase, amino acid dehydrogenase, glyceraldehyde 3-phosphoric acid dehydrogenase, 3-hydroxysteroid dehydrogenase, diaphorase, cytochrome oxidoreductase, catalase, peroxidase, glutathione reductase, and the like. Among others, the enzyme is preferably a saccharide oxidoreductase. Examples of the saccharide oxidoreductase include: glucose oxidase (GOD), galactose oxidase, glucose dehydrogenase (GDH), fructose dehydrogenase, and sorbitol dehydrogenase.

Further, the oxidoreductase can contain at least one of pyrroloquinoline quinone (PQQ) and flavin adenine dinucleotide (FAD), as a catalytic subunit and a catalytic domain. Examples of oxidoreductases containing PQQ include PQQ glucose dehydrogenase (PQQGDH). Examples of oxidoreductases containing FAD include cytochrome glucose dehydrogenase (Cy-GDH) and glucose oxidase (GOD), having an α-subunit containing FAD. In addition, the oxidoreductase can contain an electron transfer subunit or an electron transfer domain. Examples of the electron transfer subunit include a subunit containing heme which has a function of giving and receiving electrons. Examples of the oxidoreductase having the subunit containing heme include those containing cytochrome. For example, a fusion protein of glucose dehydrogenase or PQQGDH with cytochrome can be used.

In addition, examples of enzymes containing an electron transfer domain include cholesterol oxidase and quinoheme ethanol dehydrogenase (QHEDH (PQQ Ethanol dh)). As the electron transfer domain, it is preferred to use a domain containing cytochrome containing heme which has a function of giving and receiving electrons. Examples thereof include "QHGDH" (fusion enzyme; GDH with heme domain of QHGDH)), sorbitol dehydrogenase (Sorbitol DH), D-fructose dehydrogenase (Fructose DH), glucose-3-dehydrogenase derived from *Agrobacterium tumefasience* (G3DH from *Agrobacterium tumefasience*), and cellobiose dehydrogenase. The fusion protein of PQQGDH with cytochrome, which is an example of the above mentioned subunit containing cytochrome, and a cytochrome domain of PQQGDH, which is an example of the domain containing cytochrome, are disclosed, for example, in WO 2005/030807. Further, as the oxidoreductase, it is preferred to use an oligomeric enzyme including at least a catalytic subunit and a subunit containing cytochrome containing heme which has a function as an electron acceptor.

(Crosslinking Agent)

Examples of crosslinking agents include aldehyde group-containing compounds, carbodiimide group-containing compounds, maleimide group-containing compounds, oxazoline group-containing compounds and epoxy group-containing compounds. Examples of aldehyde group-containing compounds as crosslinking agents include glutaraldehyde, formaldehyde, malonaldehyde, terephthalaldehyde, isobutyraldehyde, valeraldehyde, isovaleraldehyde, cinnamaldehyde, nicotinaldehyde, glyceraldehyde, glycoaldehyde, succinaldehyde, adipaldehyde, isophthalaldehyde, terephthalaldehyde, and the like. Examples of carbodiimide group-containing compounds include hexamethylene diisocyanate, hydrogenated xylylene diisocyanate, xylylene diisocyanate, 2,2,4-trimethyl hexamethylene diisocyanate, 1,12-diisocyanate dodecane, norbornane diisocyanate, 2,4-bis-(8-isocyanate octyl)-1,3-dioctyl cyclobutane, 4,4'-dicyclohexylmethane diisocyanate, tetramethyl xylylene diisocyanate, isophorone diisocyanate, and the like. The carbodiimide group-containing compounds are commercially available under the names of: CARBODILITE™ V-02, CARBODILITE™ V-02-L2, CARBODILITE™ V-04, CARBODILITE™ V-06, CARBODILITE™ E-02, CARBODILITE™ V-01, CARBODILITE™ V-03, CARBODILITE™ V-05, CARBODILITE™ V-07 and CARBODILITE™ V-09 (all of the above are manufactured by Nisshinbo Industries, Inc.). Examples of maleimide group-containing compounds as crosslinking agents include m-maleimidobenzoyl-N-hydroxysuccinimide ester, sulfosuccinimidyl 4-(p-maleimidophenyl)butyrate, m-maleimidobenzoyl sulfosuccinimide ester, N-γ-maleimidobutyryloxy succinimide ester, succinimidyl 4-(N-maleimidomethyl)cyclohexane)1-carboxylate, N-succinimidyl-2-maleimidoacetic acid, N-succinimidyl-4-maleimidobutyric acid, N-succinimidyl-6-maleimidohexanoic acid, N-succinimidyl-4-maleimidomethyl cyclohexane-1-carboxylic acid, N-succinimidyl-4-maleimidomethyl cyclohexane-1-carboxylic acid, N-succinimidyl-4-maleimidomethyl benzoic acid, N-succinimidyl-3-maleimidobenzoic acid, N-succinimidyl- 4-maleimidophenyl-4-butyric acid, N-succinimidyl-4-maleimidophenyl-4-butyric acid, N,N'-oxydimethylene-dimaleimide, N,N'-o-phenylene-dimaleimide, N,N'-m-phenylene-dimaleimide, N,N'-p-phenylene-dimaleimide, N,N'-hexamethylene-dimaleimide, N-succinimidyl maleimide carboxylic acid, and the like. Examples of commercially available maleimide group-containing products include SANFEL BM-G (manufactured by SANSHIN CHEMICAL INDUSTRY Co., Ltd). Examples of oxazoline group-containing compounds as crosslinking agents include oxazoline compounds such as: 2,2'-bis-(2-oxazoline), 2,2'-methylene-bis-(2-oxazoline), 2,2'-ethylene-bis-(2-oxazoline), 2,2'-trimethylene-bis-(2-oxazoline), 2,2'-tetramethylene-bis-(2-oxazoline), 2,2'-hexamethylene-bis-(2-oxazoline), 2,2'-octamethylene-bis-(2-oxazoline), 2,2'-ethylene-bis-(4,4'-dimethyl-2-oxazoline), 2,2'-p-phenylene-bis-(2-oxazoline), 2,2'-m-phenylene-bis-(2-oxazoline), 2,2'-m-phenylene-bis-(4,4'-dimethyl-2-oxazoline), bis-(2-oxazolinylcyclohexane) sulfide, and bis-(2-oxazolinylnorbomane)sulfide. Further, examples of addition polymerizable oxazoline compounds include: 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl-2-oxazoline, 2-isopropenyl-5-ethyl-2-oxazoline, and the like. The compounds obtained by polymerization or copolymerization of one or more than one kind of these compounds can also be used. Examples of commercially available oxazoline group-containing compounds include Epocros WS-500, Epocros WS-700, Epocros K-1010E, Epocros K-1020E, Epocros K-1030E, Epocros K-2010E, Epocros K-2020E, Epocros K-2030E, Epocros RPS-1005 and Epocros RAS-1005 (all of the above manufactured by NIPPON SHOKUBAI Co., Ltd.); and NK linker FX (manufactured by SHIN-NAKAMURA CHEMICAL Co., Ltd.). Specific examples of epoxy group-containing compounds as crosslinking agents include sorbitol polyglycidyl ether, polyglycerol polyglycidyl ether, digylcerol polyglycidyl ether, glycerol polyglycidyl ether, trimethylolpropane polyglycidyl ether, ethylene glycol diglycidyl ether, polyethylene glycol diglycidyl ether, propylene glycol diglycidyl ether, polypropylene glycol diglycidyl ether, and the like. Two or more kinds of these compounds can be used in combination. Examples of commercially available epoxy group-containing compounds include DENACOL™ EX-611, DENACOL™ EX-612, DENACOL™ EX-614, DENACOL™ EX-614B, DENACOL™ EX-512, DENACOL™ EX-521, DENACOL™ EX-421, DENACOL™ EX-313, DENACOL™ EX-314, DENACOL™ EX-321, DENACOL™ EX-810, DENACOL™ EX-811, DENACOL™ EX-850, DENACOL™ EX-851, DENACOL™ EX-821, DENACOL™ EX-830, DENACOL™ EX-832, DENACOL™ EX-841, DENACOL™ EX-861, DENACOL™ EX-911, DENACOL™ EX-941, DENACOL™ EX-920, DENACOL™ EX-145 and DENACOL™ EX-171 (all of the above are manufactured by Nagase ChemteX Corporation); SR-PG, SR-2EG, SR-8EG, SR-8EGS, SR-GLG, SR-DGE, SR-4GL, SR-4GLS and SR-SEP (all of the above are trade names, manufactured by Sakamoto Yakuhin kogyo Co., Ltd.); and Epolite 200E, Epolite 400E and Epolite 400P (all of the above manufactured by KYOEISHA CHEMICAL Co., LTD). The type of the crosslinking agent is not limited to the above-mentioned compounds and commercially available products. The crosslinking agent may also be a compound containing at least one functional group selected from aldehyde group, maleimide group, carbodiimide group, oxazoline group and epoxy group. The form of the crosslinking agent is not limited, either and may be in the form of a monomer, polymer or the like.

(Electrically Conductive Particles)

It is preferred that the detection layer of the enzyme electrode further comprises electrically conductive particles. As electrically conductive particles, particles of a metal such as gold, platinum, silver or palladium; or a higher-order structure made of a carbon material can be used. The higher-order structure can contain, for example, one or more types of fine particles (carbon fine particles) selected from particles of electrically conductive carbon black, KETJENBLACK®, carbon nanotubeS (CNT) and fullerene.

Further, the surface of the detection layer of the enzyme electrode may be covered with an outer-layer film made of cellulose acetate and the like. Examples of raw materials for the outer-layer film, in addition to cellulose acetate, include: polyurethane, polycarbonate, polymethyl methacrylate, butyl methacrylate, polypropylene, polyether ether ketone, and the like.

(Method for Preparing Enzyme Electrode)

The enzyme electrode is prepared, for example, as follows. Specifically, a metal layer which functions as an electrode is formed on one surface of the insulating base plate. For example, a metal layer having a desired thickness (for example, about 30 nm) is formed by depositing a metallic material, by physical vapor deposition (PVD, for example, sputtering) or chemical vapor deposition (CVD), on one surface of the insulating base plate which is in the form of a film having a predetermined thickness (for example, about 100 μm). It is also possible to form an electrode layer made of a carbon material, instead of the metal layer.

Then, the detection layer is formed on the electrode. Specifically, a solution (reagent) containing the enzyme, the electrically conductive polymer, the crosslinking agent and the electrically conductive particles is prepared. The solution (reagent) is dropped on the surface of the electrode. By allowing the solution (reagent) to dry and solidify on the electrode, the enzyme electrode on the surface of which the detection layer is formed can be obtained.

The use of the enzyme electrode allows the measurement of the concentration of a substance contained in a blood sample. The substance to be measured is not particularly limited as long as it can be measured by the measuring method using the enzyme electrode. However, the substance to be measured is preferably a substance derived from a living body, which can serve as an index of a disease and/or health status, and examples thereof include glucose, cholesterol, and the like. As referred to herein a "blood sample" is a sample of untreated, i.e., whole blood, or whole blood which has been diluted or treated, but which retains red blood cells.

It is preferred that the current which is measured by the enzyme electrode is a charge transfer limiting current based on the transfer of electrons derived from the substance to the electrode. The charge transfer limiting current is a current which is generated when the electrons are transferred from the enzyme to the electrode due to the reaction between the enzyme and the substance. Further, the charge transfer limiting current is a steady-state current which does not depend on time, and preferably, a steady-state current observed after the generation of a transient current due to the charging of an electric double layer.

(Method for Producing Biosensor)

The method for producing a biosensor A according to the present invention will now be described with reference to FIG. 1. However, the following merely describes one embodiment of the present invention, and the method for producing a biosensor according to the present invention is not limited thereto.

First, four electrode patterns are printed on an insulating base plate 5, using an electrically conductive carbon ink or the like. To one of the four electrodes, a solution containing an electrically conductive polymer is added to form a hematocrit electrode 1. Further, to another one of the four electrodes, a solution containing an enzyme, the electrically conductive polymer, the crosslinking agent, and the electrically conductive particles is added to form an enzyme electrode 3. In addition, to another one of the four electrodes, a solution of silver/silver chloride is added to form a reference electrode 4. The last remaining electrode is used as it is as a counter electrode 2. Then an insulation resin is screen printed on the base plate, such that portions of these electrodes are exposed to form a reaction area 7, thereby forming an insulating layer 6.

(Method for Measuring the Concentration of Substance in Blood Sample)

The method for measuring the concentration of a substance in a blood sample according to the present invention comprises:

supplying the blood sample to a biosensor comprising the above mentioned hematocrit electrode, a working electrode, a counter electrode, a reference electrode;

measuring the value of a first current which flows when a first voltage is applied to the working electrode, and calculating the concentration of the substance from the measured value of the first current;

measuring the value of a second current which flows when a second voltage is applied to the hematocrit electrode; and correcting the concentration of the substance with the value of the second current or a hematocrit value calculated from the value of the second current.

As the second voltage, a constant voltage of 100 to 300 mV is used. The second voltage is preferably 150 to 250 mV, and particularly preferably, 200 mV.

As the first voltage, a constant voltage of 0 to 400 mV is used. The first voltage is preferably 100 to 300 mV, and more preferably, 100 to 200 mV.

Although the value of the first voltage to be applied to the working electrode and the value of the second voltage to be applied to the hematocrit electrode may be different, it is preferred that the values of the first voltage and the second voltage be the same, and be a voltage of 100 to 300 mV. If a voltage of 100 to 300 mV is used as both the first voltage and the second voltage to be applied, the application of voltage can be easily performed.

Further, although the application of the first voltage to the working electrode and the application of the second voltage to the hematocrit electrode are preferably carried out simultaneously, they may be carried out separately at different time points.

The value of the current which flows through the hematocrit electrode when a constant voltage of 100 to 300 mV is applied thereto will be negatively correlated with the hematocrit value. Accordingly, if the relationship between the value of the current which flows through the hematocrit electrode when a constant voltage of 100 to 300 mV is applied to the electrode, and the hematocrit value of the sample, is obtained in advance, the hematocrit value of the blood sample used in the measurement can be obtained from the value of the current which flows through the hematocrit electrode. This may be achieved, for example, by reference to calibration curves or use of a formula for the calculation.

The measurement of the current which flows through the hematocrit electrode is preferably carried out 3 to 60 seconds after the application of voltage.

On the other hand, by applying a constant voltage of 0 to 400 mV to the enzyme electrode, a current proportional to the concentration of the substance flows through the enzyme electrode, and thus, the value of the concentration (interim value) of the substance, such as glucose, can be obtained from the value of the current. The measurement of the current which flows through the enzyme electrode is preferably carried out 3 to 60 seconds after the application of voltage.

Further, if the relationship between the concentration of the substance and the value of the current which flows through the enzyme electrode, and the influence of the hematocrit value thereon, are obtained in advance, it is possible to accurately measure the concentration of the substance such as glucose, by correcting the value of the concentration with the hematocrit value. This may be achieved, for example, by reference to calibration curves or use of a formula for the calculation, as described in relation to the measuring apparatus described hereinafter. When the relationship between the value of the current which flows through the hematocrit electrode and the hematocrit value is known in advance, the value of the concentration of the substance may be corrected with the value of the current which flows through the hematocrit electrode, without calculating the hematocrit value.

(Method for Measuring Hematocrit Value of Blood Sample)

The method for measuring the hematocrit value of a blood sample according to the present invention comprises:

supplying the blood sample to a biosensor comprising a hematocrit electrode and an electrically conductive polymer coated on the surface of the hematocrit electrode by physical adsorption; and measuring the value of a current which flows when a voltage of 100 to 300 mV is applied to the hematocrit electrode.

If the relationship between the value of the current which flows through the hematocrit electrode when a constant voltage of 100 to 300 mV is applied to the electrode, and the hematocrit value, at respective concentrations of the substance, is obtained in advance, the hematocrit value of the blood sample used in the measurement can be obtained from the above mentioned interim value of the concentration and the value of the current which flows through the hematocrit electrode.

(Measuring Apparatus for Measuring Substance in Blood Sample)

Next, a measuring apparatus B according to the present invention will be described with reference to the drawings. Although a glucose measuring apparatus which comprises a glucose sensor as the biosensor is illustrated in this embodiment, the measuring apparatus according to the present invention is not limited to the following embodiment.

The measuring apparatus according to the present invention comprises:

the above mentioned biosensor;

a control section configured to control the application of voltage to the working electrode and the hematocrit electrode of the biosensor;

a detection section configured to measure the value of a first current which flows when a first voltage is applied to the working electrode, and the value of a second current which flows when a second voltage is applied to the hematocrit electrode;

an arithmetic section configured to calculate the concentration of a substance from the value of the first current, and to correct the concentration of the substance with the value of the second current or a hematocrit value calculated from the value of the second current; and, an output section configured to output the corrected concentration of the substance. As referred to herein, a component which is configured for a particular purpose is suitable for or adapted for that purpose.

Figure 2:
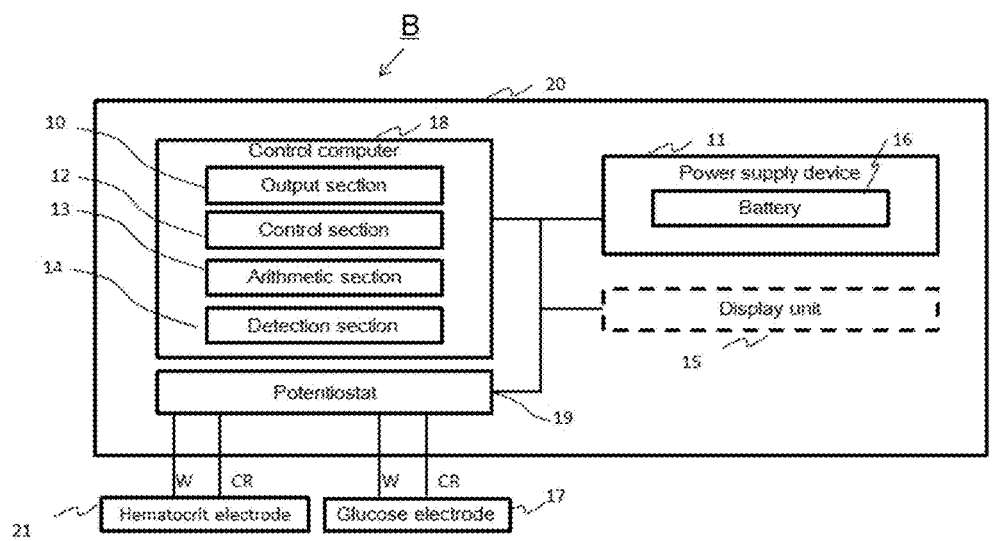
FIG. 2 is a schematic diagram illustrating one embodiment of a measuring apparatus according to the present invention.

FIG. 2 shows an example of the configuration of main electronic components included in the measuring apparatus B. A control computer 18, a potentiostat 19 and a power supply are provided on a base plate 20 housed in a housing. The control computer 18 includes, as hardware, a processor such as CPU (central processing unit); a recording medium such as a memory (RAM (Random Access Memory) or ROM (Read Only Memory)); and a communication unit. When the processor loads a program stored in the recording medium (for example, the ROM) to the RAM, and executes the program, the control computer 18 functions as an apparatus including an output section 10, a control section 12, an arithmetic section 13 and a detection section 14. The control computer 18 may also include an auxiliary memory such as a semiconductor memory (EEPROM or flash memory) or a hard disk.

The control section 12 controls the timing for applying the voltage and the value of the voltage to be applied. The power supply device 11 includes a battery 16, and supplies electricity to the control computer 18 and the potentiostat 19 for operation. It is also possible to dispose the power supply device 11 outside the housing.

The potentiostat 19 is a device which maintains the potential of the working electrode constant with respect to the potential of the reference electrode. The potentiostat 19, which is controlled by the control section 12, applies a predetermined amount of voltage between the counter electrode (reference electrode) and the working electrode of a glucose electrode (enzyme electrode) 17, and between the counter electrode and the working electrode of a hematocrit electrode 21, using terminals CRs and Ws; measures the response currents of the working electrodes which can be obtained at the terminals Ws, respectively, and send the results of the measurement to the detection section 14. The reference herein to a "glucose electrode" is an enzyme electrode in which the enzyme reacts with glucose to generate a current by transfer of electrons from the enzyme to the electrode.

The description which follows, refers to glucose as the substrate to be measured for illustration purposes. The arithmetic section 13 calculates the glucose concentration from the value of the current measured at the glucose electrode, and calculates the hematocrit value (this step can be omitted when the glucose concentration is to be corrected with the value of the current which flows through the hematocrit electrode) from the value of the current measured at the hematocrit electrode, respectively; corrects the glucose concentration with the value of the second current or the hematocrit value calculated based on the value of the second current in the arithmetic section; and stores the obtained value. The output section 10 carries out data communication between the output section 10 and a display section unit 15, and sends the calculated result of the concentration of the substance provided by the arithmetic section 13 to the display section unit 15. The display section unit 15 is capable of displaying, for example, the calculated result of the glucose concentration which is received from the measuring apparatus B, on a display screen in a predetermined format.

Figure 3:
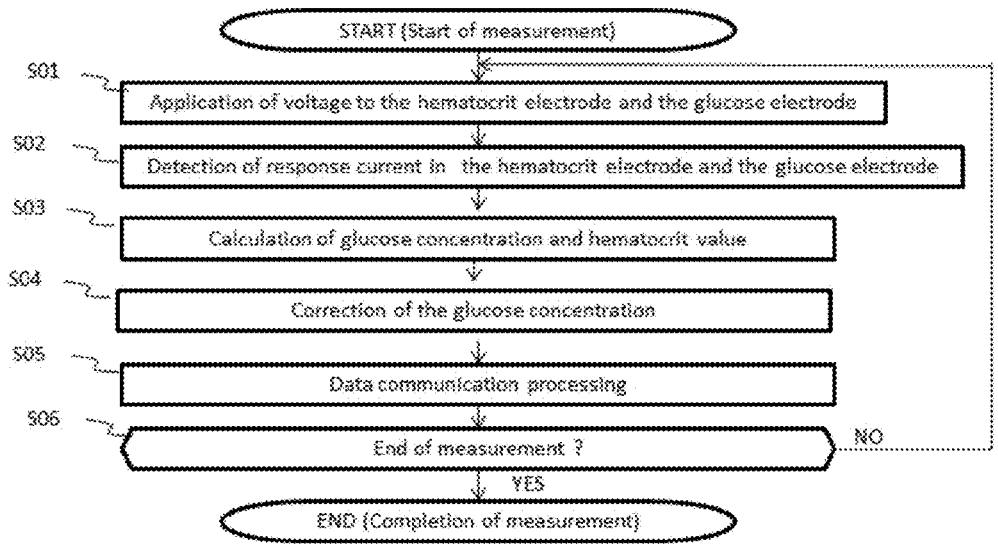
FIG. 3 is a flow chart illustrating one embodiment of a measurement program using the measuring apparatus according to the present invention.

FIG. 3 is a flow chart showing an example of the processing sequence of the glucose concentration measurement carried out by the control computer 18. When the CPU (control section 12) of the control computer 18 receives an instruction to start the measurement of the glucose concentration, the control section 12 controls the potentiostat 19 to apply the predetermined amount of voltage to each of the glucose electrode and the hematocrit electrode, and starts measuring each of the response currents (Step S01). The detection of the installation of a sensor to the measuring apparatus may be used as the instruction to start the measurement of the concentration.

Next, the potentiostat 19 measures the response current obtained by the application of voltage, specifically, the response current at the glucose electrode and the response current at the hematocrit electrode, and sends the measured current values to the detection section 14 (Step S02).

The arithmetic section 13 carries out arithmetic processing based on the current values, and calculates the glucose concentration and the hematocrit value (calculation of the hematocrit value can be omitted when the glucose concentration is to be corrected with the value of the current which flows through the hematocrit electrode) (Step S03). For example, the formulae for calculating the glucose concentration or the data of the calibration curve of the glucose concentration are preinstalled to the arithmetic section 13 in the control computer 18, and the arithmetic section 13 calculates the glucose concentration utilizing these calculation formulae or the calibration curve.

Further, the formulae or the data of the calibration curve representing the relationship between the value of current which flows through the hematocrit electrode and the hematocrit value are also preinstalled to the arithmetic section 13 in the control computer 18, and the arithmetic section 13 calculates the hematocrit value using these formulae or the data of the calibration curve and the calculated (interim) glucose concentration.

In addition, the arithmetic section 13 corrects the glucose concentration with the hematocrit value, to calculate the corrected glucose level (Step S04). For example, the formulae or the data of the calibration curve representing the relationship between the hematocrit value and the glucose concentration are preinstalled to the arithmetic section 13 in the control computer 18, and the arithmetic section 13 corrects the glucose concentration using these formulae or the data of the calibration curve.

The output section 10 sends the calculated result of the corrected glucose concentration to the display section unit 15, through a communication link provided between the output section 10 and the display section unit 15 (Step S05). Thereafter, the control section 12 determines if there are any measurement errors detected (Step S06); completes the measurement if there is no error; and displays the glucose concentration on the display section. If there are any errors, a notification of error is displayed, and then the flow sequence shown in FIG. 3 is completed.

(Apparatus for Measuring Hematocrit Value)

The apparatus for measuring a hematocrit value according to the present invention comprises:

a biosensor comprising a hematocrit electrode and an electrically conductive polymer coated on the surface of the hematocrit electrode by physical adsorption;

a control section configured to control the application of voltage to the hematocrit electrode of the biosensor;

a detection section configured to measure the value of a current which flows when a voltage is applied to the hematocrit electrode;

an arithmetic section configured to calculate a hematocrit value from the measured value of the current; and an output section configured to output the calculated hematocrit value.

EXAMPLES

Examples of the biosensor will now be described.
<Preparation of Electrodes>

Patterning was performed on one surface of a polyethylene terephthalate base material (E-22; manufactured by Toray Industries, Inc.) (length: 50 mm, width: 5 mm, thickness: 250 µm) by a screen printing method, using an electrically conductive carbon ink as a base electrode material, to form a four-electrode pattern. One of the four electrodes was left as it is to be used as a counter electrode. On the surface of another one of the four electrodes, a silver/silver chloride ink (manufactured by BAS Inc.) was coated, and the resulting base material was dried at 80° C. for 20 minutes to form a silver/silver chloride electrode, which was used as a reference electrode. Further, a reagent solution to be described later was coated on each of the remaining two electrodes, and the resulting base material was dried at 100° C. in a drying furnace for two hours to prepare a hematocrit electrode and an enzyme electrode (working electrode), respectively.

After forming the four-electrode pattern by patterning and before coating the reagent to each of the electrodes, an insulation resin polyester ink (UVF series; manufactured by Asahi Chemical Research Laboratory Co., Ltd.) was printed on top of the electrodes by screen printing to form an insulating layer, such that the insulating layer has a window which allows one portion of each of the electrodes to be exposed. Finally, a hydrophilic film, which had its thickness restricted by a double-sided adhesive tape, was pasted on top of the resulting base material and the like to form a capillary, thereby obtaining the sensor.

(Reagent Solution)

The reagent solutions as described below were prepared, and used for the above mentioned hematocrit electrode and the enzyme electrode (working electrode), respectively.
<Detection Layer Solution for Enzyme Electrode>

KETJENBLACK™ (manufactured by Mitsubishi Carbon Black): 1.20%

Electrically conductive polymer: aqueous sulfonated polyaniline solution (AQUAPASS®-01x; manufactured by Mitsubishi Rayon Co., Ltd.): 0.40%

Oxazoline group-containing polymer, EPOCROS® WS-700 (manufactured by NIPPON SHOKUBAI Co., Ltd.): 6.0%

Enzyme (Cy-GDH): 4.5 mg/mL

Phosphate buffer solution (pH 5.8): 10 mM

Sucrose: 0.5%

Here, "%" represents the percent by weight concentration of the reagent contained in the reagent solution.
<Detection Layer Solution for Hematocrit Electrode>

Electrically conductive polymer: aqueous sulfonated polyaniline solution (AQUAPASS®-01x; manufactured by Mitsubishi Rayon Co., Ltd.): 0.40%

(Cyclic Voltammetry)

Figure 4:
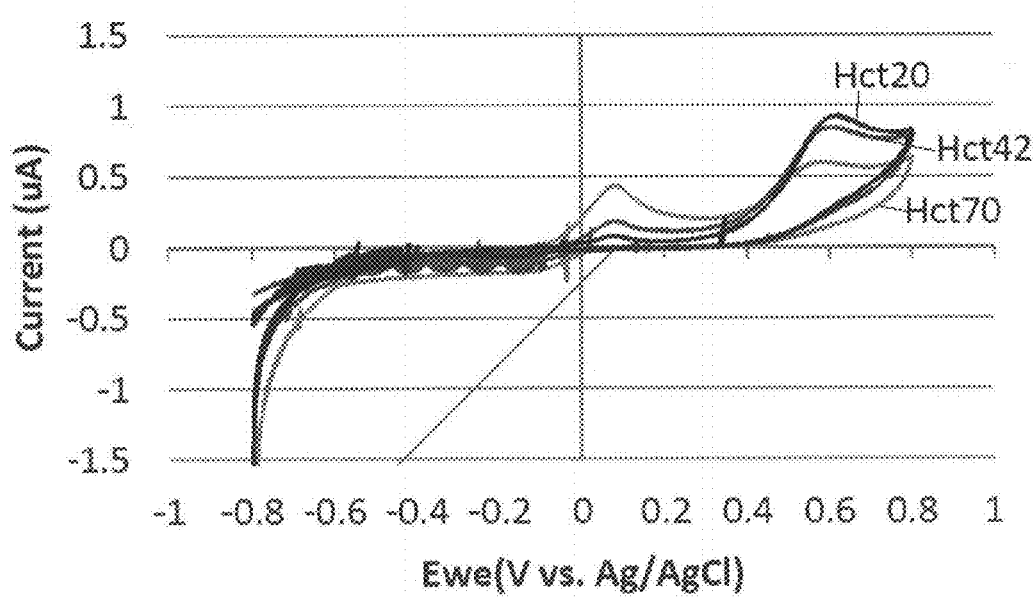
FIG. 4 is a graph illustrating the results of a cyclic voltammetry analysis of blood samples with various hematocrit values, carried out using the biosensor according to one embodiment of the present invention.
Figure 5:
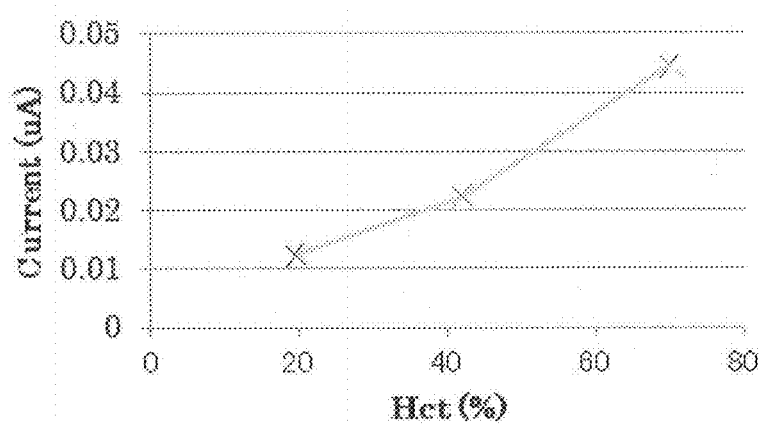
FIG. 5 is a graph illustrating the relationship between the hematocrit value and the current when a voltage of 200 mV was applied to a hematocrit electrode.

The cyclic voltammetry waveforms were analyzed to evaluate the response characteristics of the hematocrit electrode of the biosensor. The cyclic voltammetry waveforms were obtained as follows: whole blood samples having a glucose concentration of 0 mg/dL and a hematocrit value of 20%, 42% and 70% were each introduced into a sample supplying portion (reaction area), then the applied voltage was swept from −800 mV→+800 mV, at a sweep rate of 20 mV/sec, and the response current during the sweeping was measured. FIG. 4 shows the cyclic voltammetry waveforms obtained by the measurement. The result of the measurement revealed that, when the applied voltage is around 200 mV, the value of the current varies depending on the hematocrit value. FIG. 5 illustrates the relationship between the current value and the hematocrit value, when a voltage of 200 mV was applied to the hematocrit electrode. It can be seen from FIG. 5 that the current value is positively correlated with the hematocrit value, when the applied voltage is 200 mV. The reason for this is thought to be because the electrically conductive polymer receives the electrons of blood cells and transfer the electrons to the electrode, and accordingly, the current correlated with the hematocrit value flows through the electrode.

When the measurement was performed with a biosensor in which no electrically conductive polymer was included in the hematocrit electrode or in which the electrically conductive polymer was immobilized on the electrode surface by a crosslinking agent, the value of the current when a voltage of 200 mV was applied did not vary depending on the hematocrit value (not shown).

Figure 6:
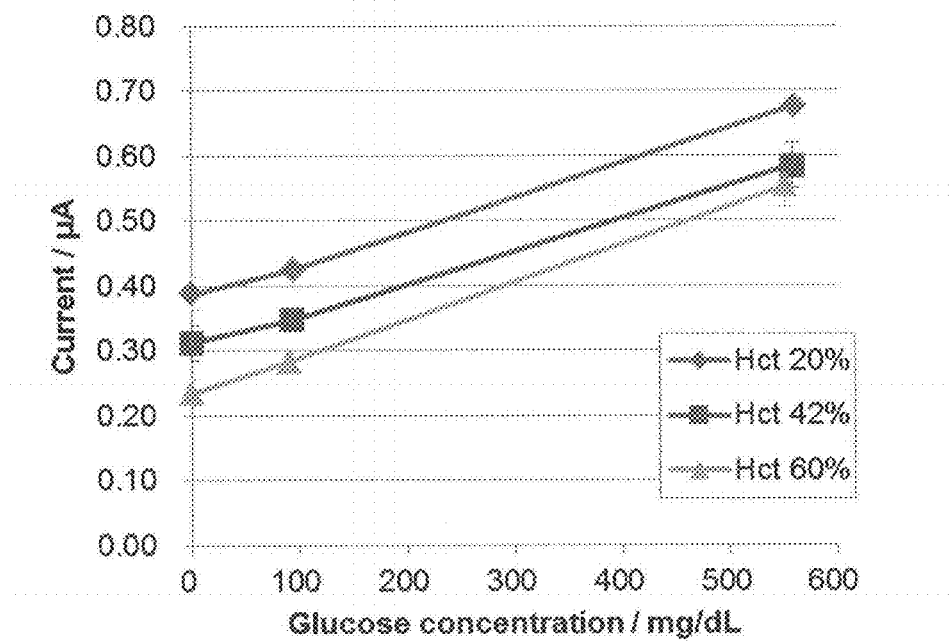
FIG. 6 is a graph illustrating the relationship between the value of the current flowing through an enzyme electrode and the glucose concentration, in samples with various hematocrit values.

FIG. 6 shows the relationship between the value of the current flowing through the enzyme electrode and the glucose concentration in samples with various hematocrit values, obtained by a separate measurement. The hematocrit value can be calculated from the value of the current flowing through the hematocrit electrode; and based on the thus obtained hematocrit value, and the value of the current flowing through the enzyme electrode, a glucose concentration corrected with the hematocrit value can be calculated.

DESCRIPTION OF SYMBOLS

A biosensor
1 hematocrit electrode
2 counter electrode
3 enzyme electrode
4 reference electrode
5 base plate
6 insulating layer
7 reaction area
B measuring apparatus
10 output section
11 power supply device
12 control section
13 arithmetic section
14 detection section
15 display section unit
16 battery
17 glucose sensor
18 control computer
19 potentiostat
20 base plate
21 hematocrit electrode
CR, W terminals While the invention has been described in detail with reference to preferred embodiments thereof, it will be apparent to one skilled in the art that various changes can be made, and equivalents employed, without departing from the scope of the invention. Each of the aforementioned documents as well as JP2015-077652 is incorporated by reference herein in its entirety.

What is claimed is:

1. A biosensor comprising:
an enzyme electrode containing a detection layer, the detection layer comprising an enzyme, an electrically conductive polymer and a crosslinking agent;
a counter electrode;
a reference electrode; and
a hematocrit electrode configured to measure a hematocrit value in a blood sample, wherein:
the electrically conductive polymer is physically adsorbed as a coating on a surface of the hematocrit electrode via a non-covalent bond,
the electrically conductive polymer is configured to transfer electrons received from the blood sample to the electrode,
the crosslinking agent contains at least one functional group selected from the group consisting of an aldehyde group, a maleimide group, a carbodlimide group, an oxazoline group, an epoxy group and combinations thereof, and
the coating does not contain a crosslinking agent.

2. The biosensor according to claim 1, wherein the electrically conductive polymer is a water-soluble electrically conductive polymer.

3. The biosensor according to claim 1, wherein the enzyme is an oxidoreductase.

4. The biosensor according to claim 1, wherein the enzyme is a saccharide oxidoreductase.

5. The biosensor according to claim 1, wherein the detection layer further comprises electrically conductive particles.

6. A measuring apparatus comprising:
the biosensor according to claim 1; and
a control section configured to control the application of voltage to the enzyme electrode and the hematocrit electrode of the biosensor,
wherein the hematocrit value is determined from a measured value of a current which flows after a voltage is applied to the hematocrit electrode.

7. A method for measuring a hematocrit value of a blood sample, comprising:
supplying the blood sample to the biosensor according to claim 1; and
measuring the value of a current which flows when a voltage of 100 to 300 mV is applied to the hematocrit electrode.

8. A measuring apparatus comprising:
the biosensor according to claim 1; and
a control section configured to control the application of voltage to the hematocrit electrode of the biosensor,
wherein the hematocrit value is determined from a measured value of a current which flows after a voltage is applied to the hematocrit electrode.

9. The biosensor according to claim 1, wherein the electrically conductive polymer is polyaniline.

10. A method for measuring the concentration of a substance in a blood sample, comprising:
supplying the blood sample to the biosensor according to claim 9;
measuring the value of a first current which flows when a first voltage of 0 to 400 mV is applied to the enzyme electrode, and calculating the concentration of the substance from the measured value of the first current;
measuring the value of a second current which flows when a second voltage of 100 to 300 mV is applied to the hematocrit electrode; and
correcting the concentration of the substance with the value of the second current or the hematocrit value calculated from the value of the second current.

11. The method according to claim 10, wherein the substance is glucose.

12. The method according to claim 10, wherein the first voltage is 100 to 200 mV and the second voltage is 150 to 250 mV.

* * * * *